US012653718B2

(12) United States Patent
Bernau et al.

(10) Patent No.: US 12,653,718 B2
(45) Date of Patent: Jun. 16, 2026

(54) OPHTHALMOLOGICAL PATIENT INTERFACE

(71) Applicant: Ziemer Ophthalmic Systems AG, Port (CH)

(72) Inventors: Werner Bernau, Köniz (CH); Fabian Müller, Biel (CH); Christian Rathjen, Bremen (DE); Michael Steinlechner, Zurich (CH); Thomas Studer, Muntelier (CH)

(73) Assignee: Ziemer Ophthalmic Systems AG, Port (CH)

( * ) Notice: Subject to any disclaimer, the term of this patent is extended or adjusted under 35 U.S.C. 154(b) by 282 days.

(21) Appl. No.: 18/375,576

(22) Filed: Oct. 2, 2023

(65) Prior Publication Data

US 2024/0108509 A1 Apr. 4, 2024

(30) Foreign Application Priority Data

Oct. 4, 2022 (CH) ................................ 001157/2022

(51) Int. Cl.
*A61F 9/009* (2006.01)
*A61B 17/30* (2006.01)

(52) U.S. Cl.
CPC ........ *A61F 9/009* (2013.01); *A61B 2017/306* (2013.01)

(58) Field of Classification Search
CPC .............. A61F 9/009; A61B 2017/306; A61B 2017/308
USPC ...................................................... 606/4, 166
See application file for complete search history.

(56) References Cited

U.S. PATENT DOCUMENTS

| | | | | |
|---|---|---|---|---|
| 2002/0103482 A1* | 8/2002 | Scholler | ................. | A61F 9/009 |
| | | | | 606/5 |
| 2013/0338649 A1* | 12/2013 | Hanebuchi | .............. | A61F 9/009 |
| | | | | 606/4 |
| 2014/0222050 A1* | 8/2014 | Heitel | .................... | A61F 9/009 |
| | | | | 606/166 |

(Continued)

FOREIGN PATENT DOCUMENTS

| | | |
|---|---|---|
| DE | 102014225635 A1 | 6/2016 |
| EP | 1306068 A2 | 5/2003 |

(Continued)

OTHER PUBLICATIONS

Feb. 6, 023—(CH) Search Report—App 001157/2022.

*Primary Examiner* — Ahmed M Farah
(74) *Attorney, Agent, or Firm* — Banner & Witcoff, Ltd.

(57) ABSTRACT

The present disclosure relates to an ophthalmological patient interface for application to an eye of a person, the ophthalmological patient interface comprising a coupling portion configured to be arranged on an application head of an ophthalmological laser treatment system, wherein the ophthalmological patient interface further comprises an eye fixation portion configured to be arranged on the eye, wherein the eye fixation portion comprises a cornea contacting element, configured to contact at least partially the cornea of the eye, and a sclera contacting element, configured to contact at least partially the sclera of the eye, wherein the cornea contacting element and the sclera contacting element define a rotationally asymmetric contact surface configured to contact the eye.

15 Claims, 6 Drawing Sheets

(56)     References Cited

U.S. PATENT DOCUMENTS

2017/0290703 A1 * 10/2017  Teuma .................... A61F 9/009
2020/0330276 A1 * 10/2020  Rathjen .............. A61F 9/00827

FOREIGN PATENT DOCUMENTS

EP           3323393 A1     5/2018
EP           3725277 A1 * 10/2020   ............. A61F 9/008

* cited by examiner

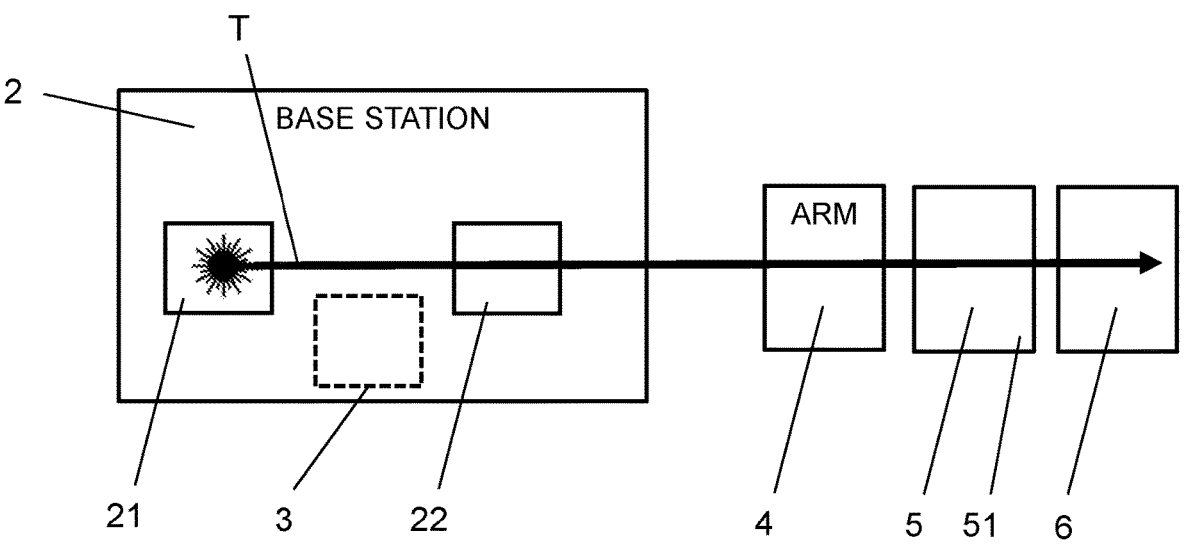
Fig. 3
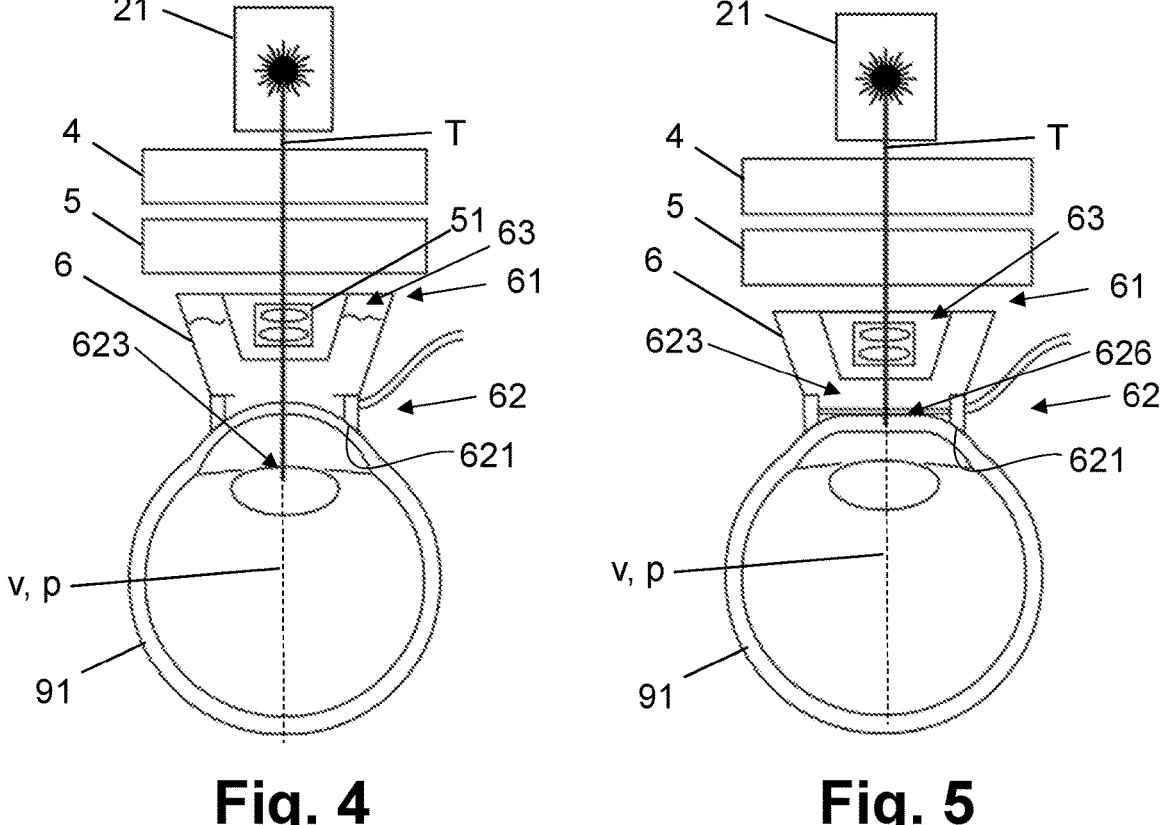
Fig. 4          Fig. 5

OPHTHALMOLOGICAL PATIENT INTERFACE

CROSS-REFERENCE TO RELATED APPLICATIONS

The present application claims priority to and the benefit of Switzerland Application 001157/2022 filed Oct. 4, 2022, which is incorporated by reference in its entirety herein.

FIELD OF THE DISCLOSURE

The present disclosure relates to an ophthalmological patient interface for application to an eye of a person. In particular, the present disclosure relates to an ophthalmological patient interface for application to an eye of a person, wherein the ophthalmological patient interface comprises a coupling portion and an eye fixation portion.

BACKGROUND OF THE DISCLOSURE

Ophthalmological treatment devices, which use a laser for eye treatment, are known. The ophthalmological treatment device has a laser source, which produces a pulsed laser beam. Additionally, the wavelength of the laser light produced by the ophthalmological treatment device is dependent on the type of eye treatment and is typically in the ultraviolet (190 nm to 230 nm) or infrared (780 nm to 1100 nm) range.

The laser beam is typically produced by a laser source arranged in a base station. The laser beam is then guided along a beam path to an application head, where the laser beam is focused onto a patient's eye.

The application head can be movably connected to the base device, for example by way of an articulated arm, wherein the articulated arm may simultaneously serve for optical beam guidance from the laser light source to the application head. Moreover, there are devices in which the application head is integrated into the base instrument or in which other device arrangements are provided.

Mechanical and optical coupling of the application head to the patient eye, for example to the cornea of the patient eye, is carried out by way of a patient interface, wherein the patient interface may comprise a transparent contact body, through which the laser pulses emerging from the projection lens are guided and which, by way of the mechanical contact with the cornea, fixes the latter with respect to the patient interface and the projection lens.

As an alternative to coupling by means of a contact body, provision can be made of liquid coupling, wherein a coupling liquid, for example a physiological saline solution, is situated between the cornea and the projection lens. The patient interface can be coupled to the patient eye by means of a negative-pressure cavity of the patient interface. The negative-pressure cavity is conventionally realized by a suction ring that is placed onto the cornea. Most suction rings have two sealing lips, which are attached to the cornea. Furthermore, there are variants which only have one ring and which generate a vacuum/negative pressure over the whole eye. In the known systems, the patient interface is coupled to the application head by means of e.g. a screw-in connection, bayonet closures or vacuum couplings.

The outer surface of the human eye, in particular the cornea and the area around the cornea are approximatively rotationally symmetric with respect to the optical axis of the eye. The conventional patient interfaces and in particular the eye contact surface of the conventional patient interfaces are therefore also rotationally symmetric such that the patient interface can be arranged coaxially on the cornea of the eye with respect to the optical axis of the eye for the desired rigid docking of the patient interface on the eye. At least one axis of the patient interface is thereby arranged coaxially with respect to the optical axis of the eye. Conventionally it is of high importance to position the patient interface coaxially with respect to the optical axis of the eye for determining the right position of the cutting pattern for the desired treatment of the eye. Nevertheless, the conventional positioning the patient interface limits the possible treatment surface of the eye for the treatment laser beam. Due to the design of the conventional patient interfaces it is almost not possible to treat portions of the eye, which are not arranged within a few millimeters of the optical axis of the eye. To increase the effective area, mirror elements are known, which are arranged in or next to the patient interface to deflect the laser beam and to direct the laser beam to the desired position. Nevertheless, the mirror elements do not increase the treatment surface; they only change the angle of incidence of the treatment laser beam.

SUMMARY OF THE DISCLOSURE

It is an object of the present disclosure to provide an ophthalmological patent interface for application to an eye of a person. In particular, it is an object of the present disclosure to provide an ophthalmological patient interface, which does not have at least some of the disadvantages of the prior art.

According to the present disclosure, these objects are addressed by the features of the independent claims. In addition, further advantageous embodiments follow from the dependent claims and the description.

According to the present disclosure, an ophthalmological patient interface for application to an eye of a person is specified. The ophthalmological patient interface comprises a coupling portion configured to be arranged on an application head of an ophthalmological laser treatment system and an eye fixation portion configured to be arranged on the eye. The eye fixation portion comprises a cornea contacting element, configured to contact at least partially the cornea of the eye, and a sclera contacting element, configured to contact at least partially the sclera of the eye, wherein the cornea contacting element and the sclera contacting element define/determine a rotationally asymmetric contact surface of the eye fixation portion configured to contact the eye. In other words, the cornea contacting element and the sclera contacting element comprise the rotationally asymmetric contact surface, which is configured to contact the eye. The ophthalmological patient interface further comprises a through opening, extending through the coupling portion and the eye fixation portion, wherein the through opening is configured to enable a treatment laser beam from the application head to pass through the ophthalmological patient interface to penetrate a target volume of tissue of the eye. Penetration of the target volume of tissue of the eye comprises for example to apply/direct the treatment laser beam on a surface of the eye, for example on the outer surface of the sclera, or to apply/direct the treatment laser beam into interior portions of the eye, for example in the cornea or the lens of the eye. Penetration further includes to form or to "drill" holes in the eye of the person and to form cuts in the eye, to cut parts of the eye of the person via the treatment laser beam. The rotationally asymmetric contact surface provides the possibility to apply the ophthalmological patient interface non-coaxially with the optical axis of the eye. The ophthalmological patient interface can be placed laterally next to the optical axis of the eye, which substantially increases the possible treatment surface for the treatment laser beam.

Rotational symmetry, also known as radial symmetry, in geometry, is the property a shape has when it looks the same after some rotation by a partial turn. Rotational asymmetry on the contrary is, according to the present disclosure, the property a shape has when it looks not the same after some rotation by a partial turn. Certain geometric objects are partially symmetrical, but still rotational asymmetric, when rotated at certain angles such as squares rotated 90°, however the only geometric objects that are truly rotationally symmetric at any angle are spheres, circles, spheroids and solids of revolution.

The optical axis of the eye is for example the straight line between the centers of curvature of refractive surfaces of the eye. The optical axis of the eye may further be the visual axis of the eye, which runs from the fovea centralis of the eye through the nodal point of the eye to the object of fixation. The optical axis of the eye may further be the line of sight of the eye, which is the straight line between the pivot point of the eye and the fixation object. The optical axis of the eye may further be the pupil axis, which is the straight line between the center of the cornea and the center of the pupil. Angular deviations of this axis are usually less than 5 degrees. The optical axis may further be a geometrical combination (best fit) between two or more of the above-mentioned different axis of the eye.

In an embodiment, the contact surface has a circular outer contour, and the rotational asymmetry of the contact surface is determined by the arrangement of the cornea contacting element and the sclera contacting element within the circular outer contour. In this embodiment, the rotational asymmetry is determined for example by the shape of the cornea contacting element and the shape of the sclera contacting element. For example, the cornea contacting element has a quarter ring shape having a first thickness and the sclera contacting element has a three-quarter ring shape having a second thickness, which differs from the first, thereby forming the rotational asymmetric contact surface.

In an embodiment, the cornea contacting element comprises a rotationally asymmetric suction opening configured to be fluidically connected to a negative pressure, such that the ophthalmological patient interface is firmly positioned on the eye, when the ophthalmological patient interface is applied on the eye and the negative pressure is provided on the suction opening. In this embodiment, the rotational asymmetry is determined for example by the asymmetric suction opening of the cornea contacting element, which contacts the cornea of the eye.

In an embodiment, the sclera contacting element comprises a rotationally asymmetric suction opening configured to be fluidically connected to a negative pressure, such that the ophthalmological patient interface is firmly positioned on the eye, when the ophthalmological patient interface is applied on the eye and the negative pressure is provided on the suction opening. In this embodiment, the rotational asymmetry is determined for example by the asymmetric suction opening of the sclera contacting element, which contacts the sclera of the eye, when applied on the eye.

In an embodiment, the negative pressure applied to the suction opening of the cornea contacting element is higher than the negative pressure applied to the suction opening of the sclera contacting element. The sclera tissue has different biomechanical properties compared to the cornea tissue, which results in different optimal negative pressures for coupling without harming the different eye tissues. Having different negative pressures for the different kind of suction openings creates the possibility to apply for the cornea and the sclera different pressures to achieve the desired suction effect in combination with eye protection.

In an embodiment, the suction openings of the cornea contacting element has a partial-ring-shape. In a further embodiment, the suction opening of the sclera contacting element has a partial-ring-shape. A partial ring or a sub-ring is a partition of a ring, for example a quarter, a third or two thirds of a ring.

In an embodiment, the suction opening of the cornea contacting element is configured to be positioned entirely on the cornea of the eye, when applied on the eye. According to this embodiment, the suction opening of the cornea contacting element has preferably a shape which, corresponds to the shape of the cornea, in particular which corresponds to the shape of the specific area of the cornea.

In an embodiment, the suction opening of the sclera contacting element is configured to be positioned entirely on the sclera of the eye, when applied on the eye. According to this embodiment, the suction opening of the sclera contacting element has preferably a shape, which corresponds to the shape of the sclera, in particular which corresponds to the shape of an area of the sclera onto which the sclera contacting element is applicable.

In a further embodiment, the suction opening of the cornea contacting element and/or the suction opening of the sclera contacting element extend on the cornea and the sclera respectively. According to this embodiment, the suction opening of the cornea contacting element is configured to be arranged on the cornea and the sclera, preferably for the most part on the cornea, and the suction opening of the sclera contacting element is configured to be arranged on the sclera and the cornea, preferably for the most part on the sclera.

In an embodiment, the through opening is configured to be at least partially filled with a coupling liquid, wherein the cornea contacting element and/or the sclera contacting element comprises a sealing or a plurality of seals or sealings. Wherein the sealing is configured to seal at least partially between the surface of the eye and the ophthalmological patient interface when the ophthalmological patient interface is applied on the eye. In an embodiment, the sealing comprises a sealing lip or a balloon seal or a sealing gel. The sealing is preferably arranged on the transition portion between the sclera and the cornea, preferably partially on the ring shaped contact surface, for example, between the suction opening of the cornea contacting element and the suction opening of the sclera contacting element. In a further embodiment, the sealing comprises a membrane, which is configured to absorb coupling liquid to provide the required sealing properties.

In an embodiment, the through opening functions as a reservoir for the coupling liquid. In a further embodiment, the coupling liquid is a physiological saline solution.

In an embodiment, the ophthalmological patient interface comprises a filling possibility, for example a connection to a liquid dispenser, which is configured to dispense coupling liquid into the through opening. In a further embodiment, the filling possibility is an opening arranged laterally on the ophthalmological patient interface, for example an opening in the eye fixation portion and/or in the coupling portion, which is accessible for the liquid dispenser even when the ophthalmological patient interface is applied on the eye and when the application head is arranged on the coupling portion of the ophthalmological patient interface.

In an embodiment, the through opening defines an opening in the eye fixation portion which is enclosed by the sealing and/or the suction opening(s).

In an embodiment, the cornea contacting element and/or the sclera contacting element comprises protrusions, which are configured to penetrate tissue of the sclera or the cornea respectively. In an embodiment, the protrusions are spike shaped and extend from the rotationally asymmetric contact surface. The protrusions have for example a pyramid shape. In a further embodiment, the protrusions are arranged only partially along the cornea-contacting element and/or the sclera-contacting element. In a further embodiment, the protrusions are arranged only on the sclera-contacting element. The sclera tissue is relatively soft compared to the cornea tissue, which is advantageous for the required penetration of the spikes in the sclera tissue to position the ophthalmological patient interface rigidly on the eye.

In an embodiment, the sealing is arranged radially outside with respect to other parts or portions of the ophthalmological patient interface, in particular radially outside of the protrusions or the suction openings. In a further embodiment, the sealing is arranged ring shaped around the rotationally asymmetric contact surface. The sealing is advantageous reliable and simple in case the sealing is arranged uninterrupted, continuously around the rotationally asymmetric contact surface.

In an embodiment, the eye fixation portion comprises a flat contact body arranged in in the through opening, wherein the contact body is at least partially transparent for the treatment laser beam to enable the penetration by the treatment laser beam of the target volume of tissue of the eye, wherein the flat contact body comprises a flat contact surface, which forms part of the rotationally asymmetric contact surface and which is configured to conform the sclera and/or the cornea of the eye. In other words, the flat contact surface deforms the sclera and/or the cornea of the eye, in case the flat contact body contacts the eye.

In an embodiment, the cornea contacting element comprises a form-fitted contact body comprising a form-fitted contact surface forming part of the rotationally asymmetric contact surface, wherein the form-fitted contact surface is form-fitted to a shape of the outer surface of the cornea of the eye, wherein the form-fitted contact surface is configured to be at least partially in form-fitting contact with the cornea of the eye for firmly positioning the ophthalmological patient interface on the eye. The surface tension of the tear film provides an advantageous docking of the form-fitted contact body on the eye, which advantageously improves the docking of the entire ophthalmological patient interface on the eye. For example, the form-fitted contact surface corresponds to an asphericity of the cornea of the eye. The form fitted contact body is for example made of glass.

In an embodiment, the cornea contacting element and/or the sclera contacting element comprise at least one suction cup having a flexible contact body configured to contact the eye, thereby forming part of the rotationally asymmetric contact surface, for positioning the ophthalmological patient interface with respect to the eye. The suction cup is for example a round rubber part arranged laterally next to the eye fixation portion of the ophthalmological patient interface. The suction cup is configured to contact the eye such that the ophthalmological patient interface is arranged rigidly on the eye when applied on the eye.

In an embodiment, a bracket is arranged between the suction cup and the eye fixation portion, wherein the bracket extends from the eye fixation portion at a specific angle and at a specific length such that the suction cup is configured to contact the cornea of the eye in particular coaxially with respect to the optical axis of the eye.

In an embodiment, the sclera contacting element comprises at least one, preferably a plurality of, spoon-shaped gripper arm(s) extending from the coupling portion and/or the eye fixation portion, wherein the spoon-shaped gripper arm(s) extend arc-shaped, the arc having an eye-ball radius, from the eye fixation portion, thereby forming part of the rotationally asymmetric contact surface, for positioning the ophthalmological patient interface with respect to the eye. The spoon-shaped gripper arm(s) follow the shape of the eyeball, such that the surface tension of the tear film provides the desired rigid docking of the ophthalmological patient interface on the eye. In a further embodiment, at least one of the spoon-shaped gripper arms comprises, preferably at its tip area, a suction cup for firmly positioning the ophthalmological patient interface on the eye. In a further embodiment, at least one of the spoon-shaped gripper arms comprises at least one protrusion, which is configured to penetrate the surface of the eye for rigidly positioning/docking of the ophthalmological patient interface on the eye.

In an embodiment, the ophthalmological patient interface further comprises a safety coupling, which comprises a first part connected rigidly to the spoon-shaped gripper arm(s) and a second part connected rigidly to the eye fixation portion and/or the coupling portion, wherein the first part is connected detachable to the second part, such that the coupling opens when a force engaging on the ophthalmological patient interface reaches or surpasses a predefined threshold force.

In an embodiment, the first part and the second part of the safety coupling are connected detachable by means of magnets or by means of a vacuum or by means of a spring or by means of a detachable interlocking connection between the first part and the second part.

In an embodiment, the coupling portion and the eye fixation portion of the ophthalmological patient interface are at least two individual parts, which are configured to be coupled for forming at least partially the ophthalmological patient interface. The coupling portion and the eye fixation portion are for example coupled by a detachable interlocking connection.

In a further aspect of the present disclosure, an ophthalmological patient interface for application only on a sclera of an eye of a person is specified. The ophthalmological patient interface according to this aspect comprises a coupling portion configured to be arranged on an application head of an ophthalmological laser treatment system, and an eye fixation portion configured to be arranged on the sclera of an eye. The eye fixation portion comprises a sclera contacting element, configured to contact the sclera of the eye, wherein the sclera contacting element defines a rotationally asymmetric contact surface configured to contact the eye. Wherein the ophthalmological patient interface comprises a through opening, extending through the coupling portion and the eye fixation portion, wherein the through opening is configured to enable a treatment laser beam from the application head to pass through the ophthalmological patient interface to penetrate a target volume of tissue of the eye.

In an embodiment of the further aspect, the contact surface has a circular outer contour, and wherein the rotational asymmetry of the contact surface is determined by the arrangement and/or shape of the sclera contact surface within the circular outer contour.

In an embodiment of the further aspect, the sclera contacting element comprises a rotationally asymmetric suction opening configured to be fluidically connected to a negative pressure, such that the ophthalmological patient interface is firmly positioned on the eye, when the ophthalmological patient interface is applied on the eye and the negative pressure is provided on the suction opening.

In an embodiment of the further aspect, the sclera contacting element comprises a plurality rotationally asymmetric suction opening configured to be fluidically connected to a negative pressure. In a further embodiment, the negative pressure applied to the different suction openings varies, in particular varies in dependence of the intended position of the respective suction openings on the sclera of the eye.

In an embodiment of the further aspect, the suction openings of the sclera contacting element has a partial-ring-shape, in particular a quarter-ring shape or half-ring-shape.

In an embodiment of the further aspect, the through opening is configured to be at least partially filled with a coupling liquid, wherein at least one of: the cornea contacting element or the sclera contacting element comprises a sealing, and wherein the sealing is configured to seal between the surface of the eye and the ophthalmological patient interface when applied on the eye. The sealing comprises for example a sealing lip or a balloon seal or a sealing gel.

In an embodiment of the further aspect, the sclera contacting element comprises protrusions, which are configured to penetrate tissue of the sclera. The protrusions are for example spike shaped. The protrusions are for example arranged only partially on the sclera contacting element.

In an embodiment of the further aspect, the eye fixation portion comprises a flat contact body arranged in in the through opening, wherein the contact body is at least partially transparent for the treatment laser beam to enable the penetration of the target volume of tissue of the eye, wherein the flat contact body comprises a flat contact surface, which forms part of the rotationally asymmetric contact surface and which is configured to conform the sclera of the eye.

In an embodiment of the further aspect, the sclera contacting element comprise at least one suction cup having a flexible contact body configured to contact the eye, thereby forming part of the rotationally asymmetric contact surface, for positioning the ophthalmological patient interface with respect to the eye.

In an embodiment of the further aspect, a bracket is arranged between the suction cup and the eye fixation portion, wherein the bracket extends from the eye fixation portion at a specific angle and at a specific length such that the suction cup is configured to contact the cornea of the eye coaxially with respect to the optical axis of the eye.

In an embodiment of the further aspect, the sclera contacting element comprises at least one, preferably a plurality of, spoon-shaped gripper arm(s) extending from the coupling portion and/or the eye fixation portion, wherein the spoon-shaped gripper arm(s) extend arc-shaped having an eye-ball radius from the eye fixation portion, thereby forming part of the rotationally asymmetric contact surface, for positioning the ophthalmological patient interface with respect to the eye.

In an embodiment of the further aspect, the ophthalmological patient interface further comprises a safety coupling wherein the safety coupling comprises a first part connected rigidly to the spoon-shaped gripper arm (s) and a second part connected rigidly to at least one of: the eye fixation portion or the coupling portion, wherein the first part is connected detachable to the second part, such that the coupling opens when a force engaging on the ophthalmological patient interface reaches or surpasses a predefined threshold.

In an embodiment of the further aspect, the first part and the second part of the safety coupling are connected detachable by means of magnets or by means of a vacuum.

In an embodiment of the further aspect, the coupling portion and the eye fixation portion of the ophthalmological patient interface are at least two individual parts, which are configured to be coupled together for forming at least partially the ophthalmological patient interface.

BRIEF DESCRIPTION OF THE DRAWINGS

The herein described disclosure will be more fully understood from the detailed description given herein below and the accompanying drawings, which should not be considered limiting to the invention described in the appended claims. The drawings in which:

FIG. 3 shows schematically different components of the ophthalmological laser treatment system including the ophthalmological patient interface;

FIG. 4 shows schematically a cross section of a first conventional ophthalmological patient interface applied on an eye;

FIG. 5 shows schematically a cross section of a second conventional ophthalmological patient interface applied on an eye;

DESCRIPTION OF THE EMBODIMENTS

Reference will now be made in detail to certain embodiments, examples of which are illustrated in the accompanying drawings, in which some, but not all features are shown. Indeed, embodiments disclosed herein may be embodied in many different forms and should not be construed as limited to the embodiments set forth herein; rather, these embodiments are provided so that this disclosure will satisfy applicable legal requirements. Whenever possible, like reference numbers will be used to refer to like components or parts.

Figures 1, 2:
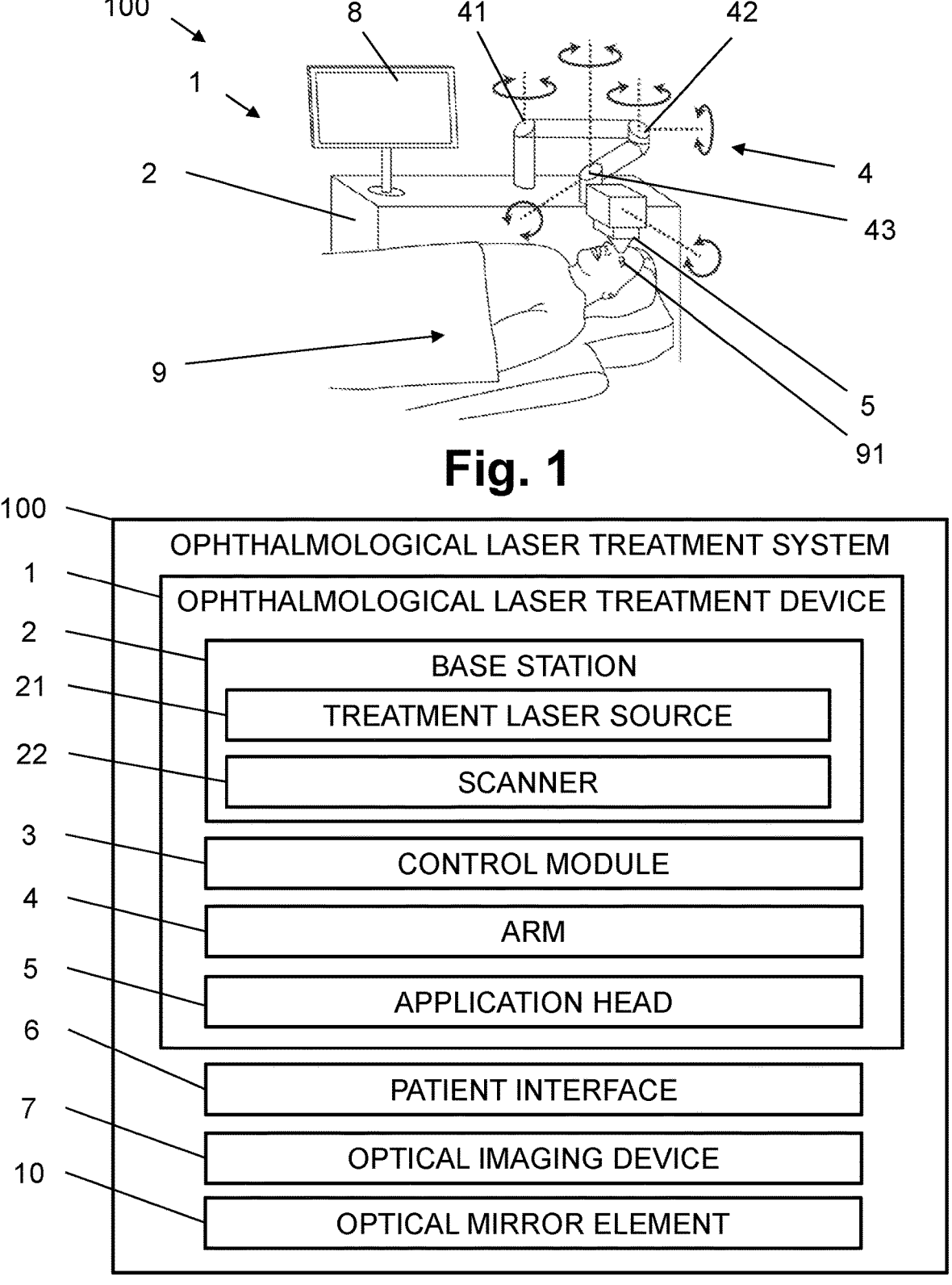
FIG. 1 shows a perspective view illustrating schematically an ophthalmological laser treatment system.
FIG. 2 shows a block diagram illustrating schematically an ophthalmological laser treatment system with an ophthalmological patient interface.

FIG. 1 shows a perspective view illustrating schematically an ophthalmological laser treatment system 100. FIG. 2 shows a block diagram illustrating schematically the ophthalmological laser treatment system 100 with an ophthalmological patient interface 6. FIG. 3 shows schematically different components of the ophthalmological laser treatment system 100 including the ophthalmological patient interface 6.

FIGS. 1 to 3 schematically illustrate modules and/or elements of various embodiments of the ophthalmological laser treatment system 100 and provide exemplary sequences or arrangement of modules and/or elements, including modules and/or elements in a beam path T. Some modules and/or elements shown in a particular figure may be combined with modules and/or elements shown in another figure.

The ophthalmological laser treatment system 100 comprises an ophthalmological laser treatment device 1 comprising a base station 2. The base station 2 is configured as a fixed or mobile apparatus. The ophthalmological laser treatment device 1 has a treatment laser source 21 arranged in the base station 2, which generates a treatment laser beam T. The base station 2 further includes, for example, a power supply and other auxiliary subsystems necessary for operation of the ophthalmological laser treatment device 1.

The treatment laser source 21 is configured, for example, to generate an ultraviolet or infrared treatment laser beam T having a wavelength of between 190 nm and 230 nm. For example, the treatment laser source 21 comprises an excimer or a solid-state laser, which produces such an ultraviolet treatment laser beam T. The excimer laser uses a combination of a noble gas and a reactive gas under high pressure and electrical stimulation to generate the treatment laser beam T. In particular, an excimer laser using argon as the noble gas and fluoride as the reaction gas may be used as the treatment laser source 21.

In an embodiment, the treatment laser beam T is a pulsed laser beam. In an embodiment, the treatment laser source 21 is configured to generate femtosecond laser pulses, which have pulse widths of typically from 10 fs to 1000 fs (1 fs=$10^{-15}$ s).

The base station 2 includes a scanner 22, which is configured to steer the treatment laser beam T delivered by the treatment laser source 21 onto or into treatment points on a treatment pattern (comprising a laser trajectory).

The ophthalmological laser treatment device 1 comprises an application head 5. The application head 5 is designed to guide the treatment laser beam T into or onto the eye 91 of a patient 9 (as shown, for example, in FIG. 1). The application head 5, for this purpose, can comprise focusing optics 51 configured to focus the treatment laser beam T onto one or more treatment points inside or on the eye 91, in particular the cornea or the sclera for a pointwise tissue disruption or ablation. The focusing optics 51 comprise a lens system having one or more optical lenses. Depending on the embodiment, the focusing optics 51 comprise one or more movable or deformable lenses and/or a drive for moving the entire focusing optics in order to set and adjust the focal depth, or the treatment height, in the projection direction along the projection axis.

The ophthalmological laser treatment system 100 comprises an ophthalmological patient interface 6. The application head 5 is preferably fixed onto the eye 91 by means of the ophthalmological patient interface 6, which is coupled to the eye for example using negative pressure. Different embodiments of the ophthalmological patient interface 6 of the present disclosure will be described in more detail with reference to FIGS. 4 to 17.

Depending on the embodiment, the ophthalmological laser treatment system 100 further comprises an optical imaging device 7 and an optical mirror element 10.

The ophthalmological laser treatment device 1 comprises an arm 4 arranged between the base station 2 and the application head 5. The arm 4 is configured to provide a beam path for the treatment laser beam T, such that the treatment laser beam T is guided along the inside of the arm 4 from the base station 2 to the application head 5. In an embodiment, the arm 4 comprises one or more joints 41 (as shown in FIG. 1) such that the application head 5 is movable and/or rotatable with respect to the base station 2. Each rotatable joint 41 comprises a mirror arranged in the beam path to reflect the treatment laser beam T along the arm 4.

The ophthalmological laser treatment system 100 is controlled by a control module 3, by controlling the treatment laser source 21 and the scanner 22, as well as by controlling additional modules of the ophthalmological laser treatment system 100 arranged in the beam path of the treatment laser beam T.

The ophthalmological laser treatment system 100 optionally includes a user interface comprising, for example, one or more user input devices, such as a keyboard, and one or more output devices, such as a display 8 (as shown in FIG. 1). The display 8 may also be an input device. The user interface is configured to receive user inputs from an eye treatment professional, in particular based on, or in response to, information displayed to the eye treatment professional using the one or more output devices.

FIGS. 4 and 5 show schematically a cross section of a first and second conventional ophthalmological patient interface 6 applied on an eye 91 of a person 9. FIGS. 4 and 5 show schematically the treatment laser source 21, the arm 4 and the application head 5 with the focusing optics 51. The figures further show schematically the treatment laser beam T and its beam path from the treatment laser source 21 to the eye 91. The conventional ophthalmological patient interface 6 comprises a coupling portion 61, which is configured to be attached to the application head 5, and an eye fixation portion 62, which is configured to contact the cornea of the eye 91. The eye fixation portion 62 comprises a contact surface, which is configured to contact the eye 91, when the ophthalmological patient interface 6 is applied on the eye 91. The figures further show schematically a ring shaped suction opening 621, which extends ring shaped along the entire contact surface of the eye fixation portion 62. The ring shaped suction opening is connected to a negative pressure or vacuum such that the eye fixation portion 62 is rigidly attachable to the eye 91. The Figures further show that the ophthalmological patient interface 6 comprises a through opening 63, extending through the coupling portion 61 and the eye fixation portion 62. The treatment laser beam T is guided along the through opening 63 to a treatment surface 623 on or in the cornea of the eye 91. The through opening 63 is configured to enable the treatment laser beam T from the application head 5 to pass through the ophthalmological patient interface 6 to penetrate a target volume of tissue of the eye 91. FIG. 5 additionally comprises a contact body 626, which is arranged in the through opening 63 and which is configured to conform/deform the cornea of the eye 91, for example for a conventional LASIK surgery.

FIGS. 4 and 5 further show the optical axis v of the eye 91 and an optical axis p of the ophthalmological patient interface 6. The trough opening 63 extends along the axis p. Both axes v, p are arranged coaxially with respect to each other. It is of high importance that these two axes are arranged coaxially with respect to each other for an optimal treatment result using the conventional ophthalmological patient interface 6 for the desired precise treatment. The coaxially alignment is achieved by a rotational symmetry of the contact surface of the eye fixation portion 62, which perfectly aligns with the rotational symmetric surface of the cornea of the eye 91.

Reference is now made to the embodiments of the present disclosure as shown in FIGS. 6 to 17.

Figures 6, 7, 8, 9, 10:
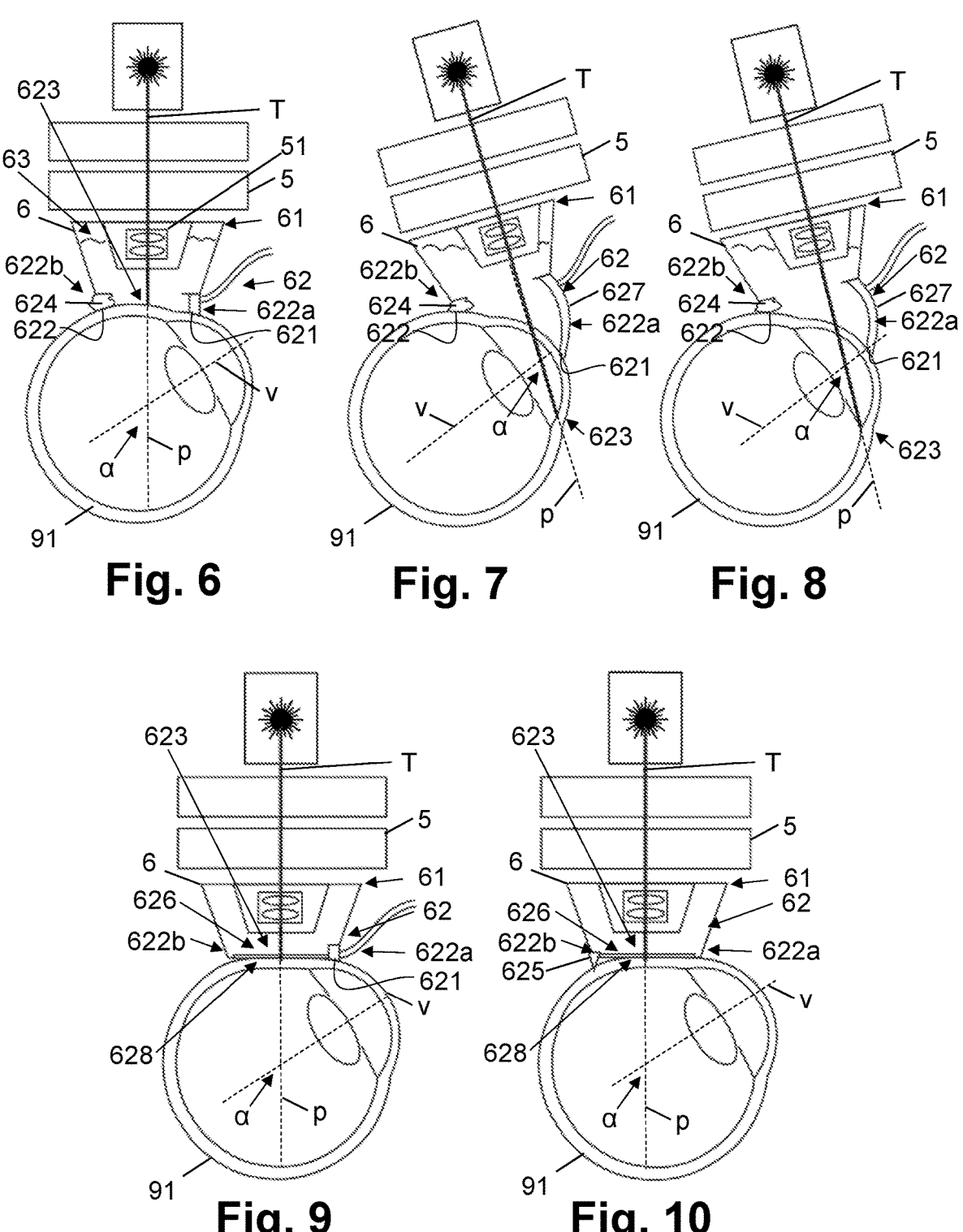
FIG. 6 shows schematically a cross section of an ophthalmological patient interface according to a first embodiment.
FIG. 7 shows schematically a cross section of an ophthalmological patient interface according to a second embodiment.
FIG. 8 shows schematically a cross section of an ophthalmological patient interface according to a third embodiment.
FIG. 9 shows schematically a cross section of an ophthalmological patient interface according to a fourth embodiment.
FIG. 10 shows schematically a cross section of an ophthalmological patient interface according to a fifth embodiment.
Figure 11:
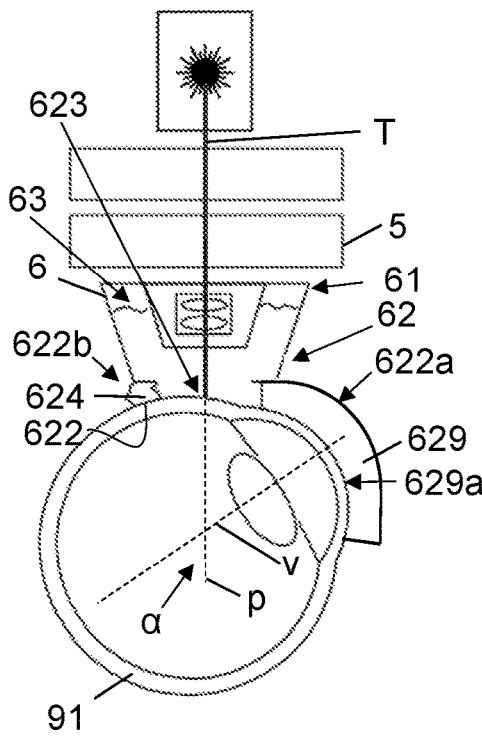
FIG. 11 shows schematically a cross section of an ophthalmological patient interface according to a sixth embodiment.
Figure 12:
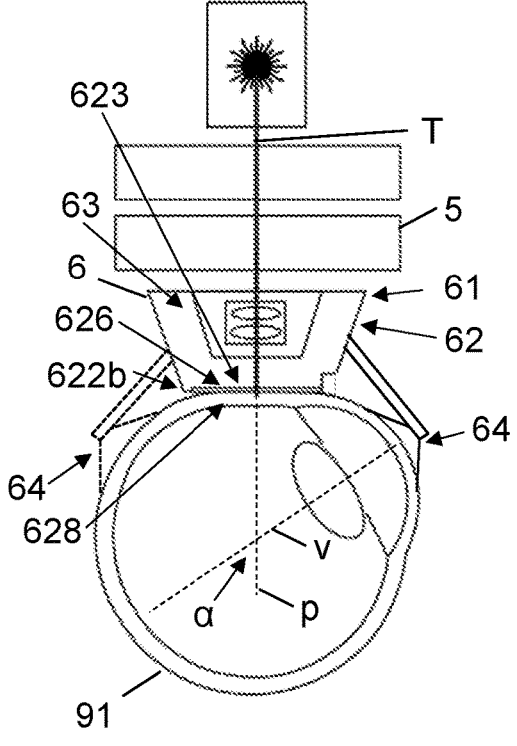
FIG. 12 shows schematically a cross section of an ophthalmological patient interface according to a seventh embodiment.

FIGS. 6 to 17 show at first sight that the ophthalmological patient interface 6 according to the present disclosure with its axis p is not configured to be arranged coaxially and is also not configured to be arranged co-linear with respect to the optical axis v of the eye 91, when applied on the eye. The axis p of the ophthalmological patient interface 6 is configured to be arranged at an inclination angle α with respect to the optical axis of the eye 91. The ophthalmological patient interface 6 is configured to be arranged laterally next to the optical axis v of the eye 91, at a different position on the almost spherical eyeball. The ophthalmological patient interface 6, according to the present disclosure, extends, due to its unique features, the possible treatment surface 623, which is reachable by the treatment laser beam T, substantially. According to the present disclosure, it is in particular possible to treat the sclera of the eye 91 by the treatment laser beam T. FIGS. 6 to 8 and 11 further indicate schematically that a coupling liquid is arranged in the through opening 63. The treatment surface 623 is according to these embodiments not deformed by the ophthalmological patient interface 6, which reduces the injury possibility due to the application of the ophthalmological patient interface 6. FIGS. 9, 10, and 12 show the ophthalmological patient interface 6 with an applanating contact body, which is configured to conform/deform the surface of the eye 91.

FIGS. 6 to 12 show different embodiments of the ophthalmological patient interface 6 according to the present disclosure. All of these figures show the treatment laser beam T, the application head 5 and the ophthalmological patient interface 6 applied on the eye 91 of a person 9. The figures further show the focusing optics 51 associated with the application head 5 and the through opening 63 extending through the coupling portion 61 and the eye fixation portion 62.

FIGS. 6 to 12 further show that the eye fixation portion 62 comprises a cornea contacting element 622a, configured to contact at least partially the cornea of the eye 91, and a sclera contacting element 622b, configured to contact at least partially the sclera of the eye 91, wherein the cornea contacting element 622a and the sclera contacting element 622b define a rotationally asymmetric contact surface 622 configured to contact the eye 91. The contact surface 622 of the eye fixation portion 62 is rotationally asymmetric such that the eye fixation portion 62 is advantageously dockable/arrangeable to the surface of the eye 91 laterally next to the optical axis v of the eye 91. The figures show that the human eye 91 has not a perfect spherical shape, the cornea of the eye 91 forms a spherical bulge or a spherical protrusion on the eyeball. The optical axis v of the eye 91 is arranged in line with the center of the bulge and the center of the eyeball. A conventional rotational symmetric patient interface, as shown in FIGS. 4 and 5, can therefore only align perfectly on the surface of the eyeball if arranged coaxially with the optical axis v of the eye 91. The rotationally asymmetry of the ophthalmological patient interface 6 according to the present disclosure enables to position the ophthalmological patient interface 6 perfectly aligned on the surface of the eye 91 at any other position, contacting the cornea, via the cornea contacting element 622a and the sclera via the sclera contacting element 622b of the eye 91. The ophthalmological patient interface 6 according to the present disclosure enables therefore for example to treat the sclera and the cornea of the eye 91.

FIG. 6 shows a first embodiment of the ophthalmological patient interface 6 according to the present disclosure. The rotational asymmetric contact surface 622 is formed by a sealing 624, which forms part of the sclera contacting element 622b, and by a suction opening 621 of the cornea contacting element 622a. In other words, the sealing 624, for example a balloon sealing, and the cornea contacting element 622a comprising the suction opening 621 form or determine the rotational asymmetric contact surface 622 of the patient interface 6 according to this embodiment. The sealing 624 is configured to seal between the sclera of the eye 91 and the eye fixation portion 62. The suction opening 621, in particular a housing of the suction opening 621, is configured to be arranged at least partially on the cornea of the eye 91 and to position the ophthalmological patient interface 6 rigidly on the eye 61. The suction opening 621 has for example a partial ring shape. The suction opening 621 is configured to be connected to a negative pressure/vacuum. According to this embodiment, the treatment laser beam T can advantageously treat the sclera of the eye 91.

FIGS. 7 and 8 show a second and third embodiment of the ophthalmological patient interface 6. FIGS. 7 and 8 differ from FIG. 6 in the shape of the eye fixation portion 62 of the ophthalmological patient interface 6, which enables to form a larger inclination angle α between the axis p and the optical axis v of the eye 91, when the ophthalmological patient interface 6 is applied on the eye 91. The rotationally asymmetric contact surface 622 of these embodiments is also formed by a sealing 624, forming the sclera contacting element 622b, and by the cornea contacting element 622a comprising one suction opening 621. The cornea contacting element 622a comprises an extension portion 627, which extends from the coupling portion 61 beyond the maximal extension of the sclera contacting element 622b. The extension portion 627 follows a radius such that the tip of the extension portion 627, which comprises the suction opening 621, is advantageously applicable on the cornea of the eye 91. The embodiments shown in FIGS. 7 and 8 differ in the length of the extension portions 627. The length of the extension portion 627 determines the inclination angle α between the axis p of the ophthalmological patient interface 6 and the axis v of the eye 91, when applied on the eye 91. The length of the extension portion 627 therefore also determines the angle of incidence of the treatment laser beam T. In FIG. 7, the treatment surface 623, which is advantageous reachable by the treatment laser beam T, using this specific ophthalmological patient interface 6, is the interior side of the ocular limbus of the eye 91. In FIG. 8, the treatment surface 623, which is advantageous reachable by the treatment laser beam T, using this specific ophthalmological patient interface 6, is the anterior chamber angle of the eye 91. The ophthalmological patient interface 6, having different lengths of the extension portion 627 is, for example, selected in dependence of the desired treatment.

FIGS. 9 and 10 show a fourth and fifth embodiment of the ophthalmological patient interface 6. These embodiments comprise a contact body 626, arranged in in the through opening 63. The contact body 626 or contact glass is at least partially transparent for the treatment laser beam T to enable the penetration of the target volume of tissue of the eye 91. The flat contact body 626 comprises a flat contact surface 628, which forms part of the rotationally asymmetric contact surface 622 and which is configured to conform the sclera of the eye 91. These embodiments do not comprise a coupling liquid arranged in the through opening 63 and also do not comprise a corresponding sealing. The fourth embodiment of FIG. 9 comprises a suction opening 621, preferably partially ring shaped and preferably partially surrounding the contact body 626, which is arranged in the cornea contacting element 622*a*. The sclera contacting element 622*b* is according to this embodiment at least partially formed by the contact body 626 and the cornea contacting element 622*a* is formed by the part which houses the suction opening 621 and also partially by the contact body 626.

The contact body 626 is, according to this embodiment, configured to contact with its flat contact surface 628 the cornea and the sclera of the eye 91.

The fifth embodiment of the ophthalmological patient interface 6 shown in FIG. 10 comprises at least one protrusion 625, which forms part of the sclera contacting element 622*b* and which is configured to penetrate tissue of the sclera of the eye 91, when the ophthalmological patient interface 6 is applied on the eye 91. The protrusions 625 are spike shaped and are arranged laterally next to the contact body 626. The protrusions 625 have for example the shape of a pyramid. The protrusions 625 advantageously help to position the ophthalmological patient interface 6 rigidly on the eye 91. Sclera tissue is relatively soft and is not easily damaged by the protrusions 625, compared to cornea tissue. Nevertheless, in a further embodiment, at least one protrusion 625 could be also arranged in the cornea contacting element 622*a* configured to penetrate the cornea of the eye 91. The protrusions 625 of the cornea contacting element 622*a* are for example smaller with respect to the protrusions 625 of the sclera contacting element 622*b*. The protrusions 625 are for example distributed unevenly around the contact surface 622, thereby forming its rotational asymmetry. In another embodiment, the protrusions 625 are evenly distributed around the rotationally asymmetric contact surface 622.

In a further embodiment, not shown in the figures, the eye fixation portion 62 may comprise protrusions 625 and at least one, preferably a plurality of suction openings 621, arranged in the sclera contacting element 622*b* and/or in the cornea contacting element 622*a*.

In a further embodiment, not shown in the figures, the contact body 626 comprises instead of the flat contact surface 628 a spherical contact surface, which corresponds to the outer non-deformed surface of the eye 91, onto which the contact body 626 is configured to be applied. The contact body 626 or the ophthalmological patient interface 6 comprising the contact body 626 is, for example, selected in dependence of the outer surface of the specific eye 91 and/or on the position onto which the ophthalmological patient interface 6 should be applied on the eye 91. This improves the alignment of the ophthalmological patient interface 6 on the eye 91.

FIG. 11 shows schematically a sixth embodiment of the ophthalmological patient interface 6 according to the present disclosure. The rotationally asymmetric contact surface 622 is formed by a sealing 624 forming part of the sclera contacting portion 622*b* and by a form fitted contact body 629 comprising a form fitted contact surface 629*a* forming part of the cornea contacting portion 622*a*. As best visible in FIG. 11, the form fitted contact body 629 extends laterally of the ophthalmological patient interface 6 next to the through opening 62 along a shape which corresponds to a negative of a cornea of the eye 91. In other words, the form fitted contact surface 629*a*, which is configured to contact the cornea of the eye 91, has at least partially the surface shape of the cornea of the eye 91. When applied on the eye, the form fitted contact surface 629*a* docks advantageously on the cornea of the eye 91, such that the ophthalmological patient interface 6 is advantageously rigidly attached to the eye 91. The surface tension of the tear film provides an advantageous docking of the form-fitted contact body 629 on the eye 91, which advantageously improves the docking of the entire ophthalmological patient interface 6 on the eye 91. In a further embodiment, the form-fitted contact surface 629*a* corresponds to an individual asphericity of the cornea of the eye 91.

FIG. 12 shows schematically a seventh embodiment of the ophthalmological patient interface 6 according to the present disclosure. The rotational asymmetric contact surface 622 is determined by a suction cup 64, which is arranged next to the treatment surface 623 and which is configured to contact the surface of the eye 91 to position the ophthalmological patient interface 6 rigidly on the eye 91. The suction cup 64 is for example a round rubber part. The suction cup 64 is preferably arranged coaxially with the optical axis v of the eye 91 on the cornea. The suction cup 64 is for example arranged on one tip of a bracket, which extends from the coupling portion 61 or the eye fixation portion 62; the other tip or end of the bracket is connected to the coupling portion 61 or the eye fixation portion 62. The bracket, in particular the bracket length and bracket angle, determines the position of the suction cup 64 with respect of the rest of the contact surface 622. The ophthalmological patient interface 6 may comprise a plurality of suction cups 64 arranged around the ophthalmological patient interface 6, having for example different brackets, for an optimized positioning of the ophthalmological patient interface 6 on the eye 91.

Figure 13:
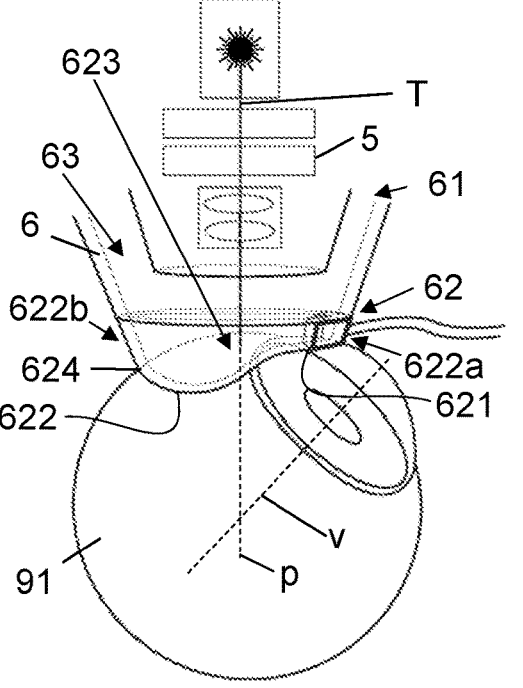
FIG. 13 shows schematically a perspective view of an ophthalmological patient interface according to an eight embodiment.

FIG. 13 shows schematically an eight embodiment of the ophthalmological patient interface 6 according to the present disclosure. FIG. 13 shows in a perspective view the ophthalmological patient interface 6 applied on the eyeball. FIG. 13 advantageously shows the rotational asymmetry of the contact surface 622 of the eye fixation portion 62. The contact surface 622 as shown in this figure is not only rotational asymmetric in a plane area but also varies in its vertical extension such that the contact surface 622 advantageously fits/advantageously touches the surface of the eye 91. The contact surface 622 according to this embodiment is formed by the eye fixation portion 62, which extends from the coupling portion 61. The extension length varies around the eye fixation portion 62, such that the contact surface 622 is applicable on the sclera and on the cornea, which extends spherical from the spherical sclera. FIG. 13 further shows that the eye fixation portion 62, in particular the cornea contacting element 622*a*, comprises a suction opening 621, which has a partial ring shape and which is connectable via a pressure line to a negative pressure. The suction opening 621 is according to this embodiment configured to be arranged on the cornea of the eye 91. In a further embodiment, the suction opening 621 might extends towards the sclera. In a further embodiment, the eye fixation portion 62, in particular the cornea contacting element 622*a* and or the sclera contacting element 622*b*, might comprise one or a plurality of suction openings 621.

Figure 14:
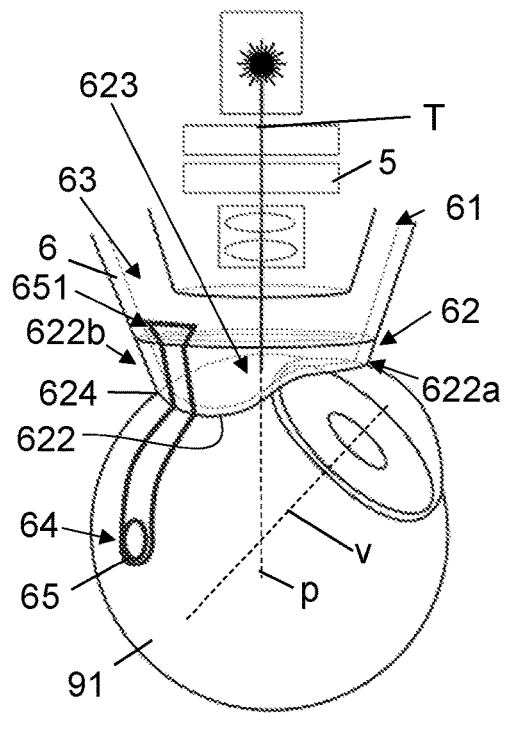
FIG. 14 shows schematically a perspective view of an ophthalmological patient interface according to a ninth embodiment.

FIG. 14 shows schematically a ninth embodiment of the ophthalmological patient interface 6 according to the present disclosure. The embodiment as shown in FIG. 14 differs from the embodiment as shown in FIG. 13 in that the eye fixation portion 62 does not comprise a suction opening. The embodiment as shown in FIG. 14 comprises a spoon shaped gripper arm 65. The spoon shaped gripper arm 65 extends from the coupling portion 61 and the eye fixation portion 62 vertically beyond the rest of the contact surface 622. The spoon shaped gripper arm 65 is configured to contact at least partially the eye 91 and forms therefore part of the rotationally asymmetric contact surface 622. The spoon shaped gripper arm 65 extends or follows along an arc, which has an eye-ball radius. In other words, the part of the spoon shaped gripper arm 65 extending beyond the rest of the contact surface 622 follows the form of the eyeball. The spoon shaped gripper arm 65 provides an advantage docking solution for docking of the ophthalmological patient interface 6 on the eye 91. The spoon shaped gripper arm 65 comprises at its tip according to this embodiment an optional suction cup 64. The embodiments of the ophthalmological patient interface 6 show that the eye fixation portion 62 and the coupling portion 61 are two separate parts, which are attached/connected with each other to form the ophthalmological patient interface 6. In FIGS. 13 and 14, this separation is indicated by a line between the two parts. FIG. 14 further shows that the spoon shaped gripper arm 65 extends along the eye fixation portion 62 and the coupling portion 62. The ophthalmological patient interface 6 as shown in FIG. 14 further comprises a safety coupling 651. The safety coupling 651 according to this embodiment is implemented between the coupling portion 61 and the eye fixation portion 62. Both parts are arranged detachable to each other, such that the safety coupling 651 opens, when a force, for example an unexpected hit by a third person, engages on the ophthalmological patient interface 6. The safety coupling 651 is configured such that it opens, when the force, which engages on the ophthalmological patient interface 6 reaches or surpasses a predefined threshold. The safety coupling 651 may comprise magnets and/or a vacuum/negative pressure and/or a spring element.

In a further embodiment, not shown in the figures, the ophthalmological patient interface 6 comprises a plurality of spoon shaped gripper arms 65, for example, two arranged on opposing sides of the ophthalmological patient interface 6. Having a plurality of the spoon shaped gripper arms 65 advantageously helps to improve the rigid positioning of the ophthalmological patient interface 6 on the eye 91.

Figure 15:
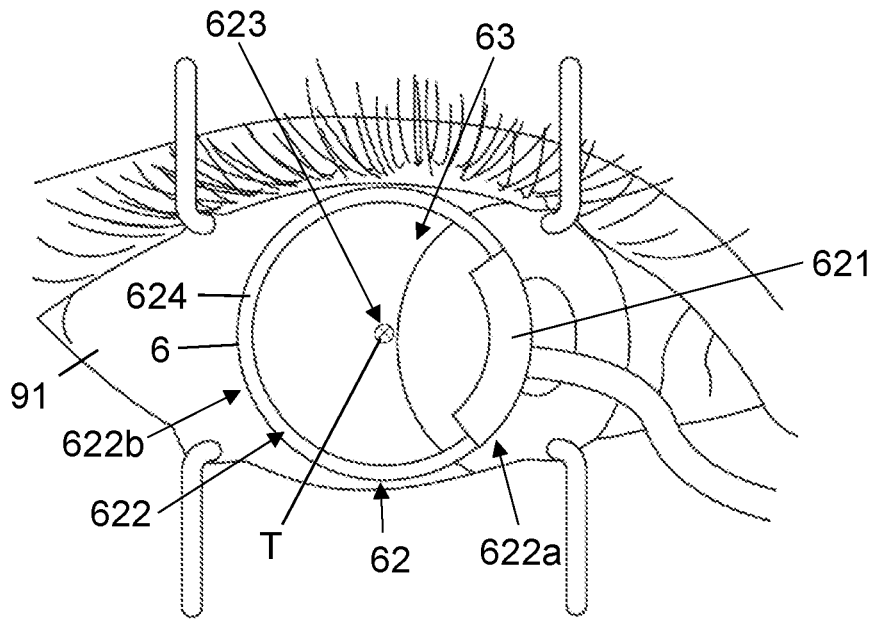
FIG. 15 shows schematically a top view of an ophthalmological patient interface according to a tenth embodiment.
Figure 16:
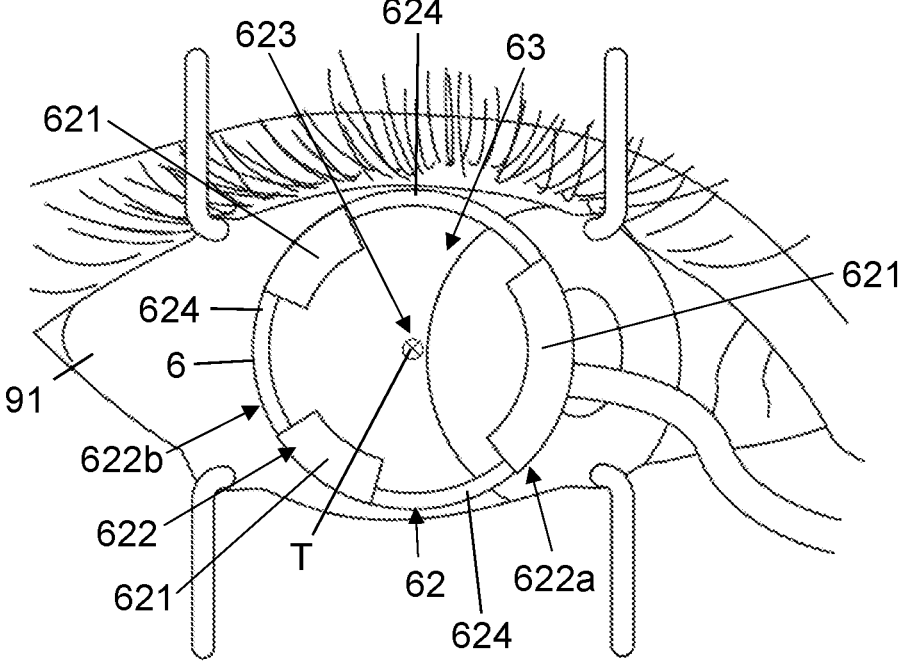
FIG. 16 shows schematically a top view of an ophthalmological patient interface according to an eleventh embodiment.
Figure 17:
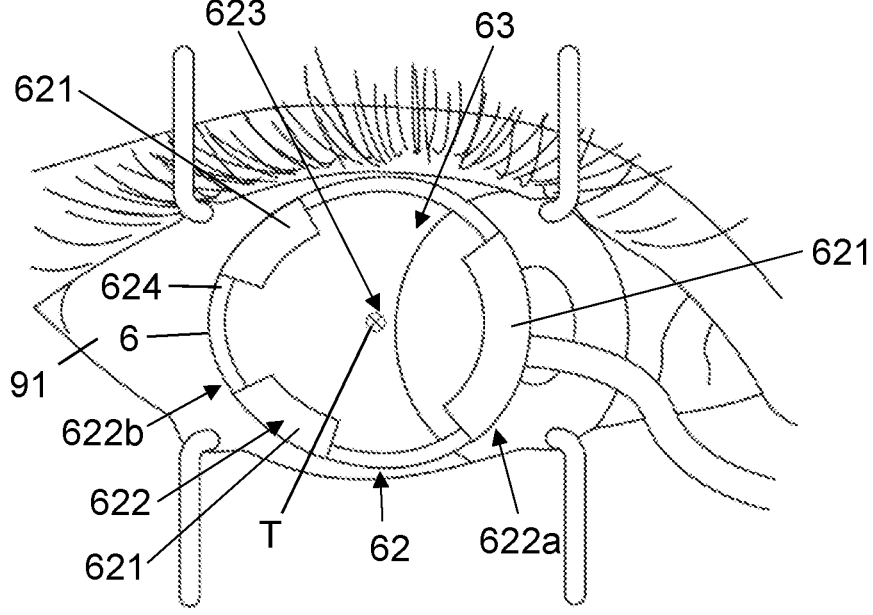
FIG. 17 shows schematically a top view of an ophthalmological patient interface according to a twelfth embodiment.

FIGS. 15, 16 and 17 show schematically a tenth, eleventh and twelfth embodiment of the ophthalmological patient interface 6 according to the present disclosure. All of these figures show a top view of the ophthalmological patient interface 6 arranged on the eye 91. The figures do not show the entire ophthalmological patient interface 6, but only show the contact surface 622 of the ophthalmological patient interface 6. FIGS. 15 to 17 advantageously show the rotational asymmetry of the contact surface 622. FIG. 15 and FIG. 16 show that the contact surface 622 has a circular outer contour. FIG. 15 further shows that the contact surface 622 comprises a suction opening 621 arranged in the cornea contacting element 622*a*, which determines the rotational asymmetry of the contact surface. The suction opening 621 as shown in FIG. 15 is arranged only in the cornea contacting element 622*a*. The sclera contacting element 622*b* of this embodiment does not comprise any suction opening. The contact surface 622 of the embodiment as shown in FIG. 15 further comprises a sealing 624, which is arranged mainly on the sclera contacting element 622*b* but also extends to the cornea contacting element 622*a*. The contact surface 622 is determined according to this embodiment by the sealing 624 and the suction opening 621.

FIG. 16 differs from FIG. 15 in that it has a plurality of suction openings 621. One is arranged in the cornea contacting element 622*a* and two are arranged in the sclera contacting element 622*b*. According to this embodiment, a sealing 624 is arranged between the suction openings 621. The negative pressure applied on the suction opening 621 of the cornea contacting element 622*a* is in an embodiment higher compared to the negative pressure applied on the suction openings 621 of the sclera contacting elements 622*b*. This is for example achieved via different negative pressure lines providing different negative pressures on the suction openings 621.

FIG. 17 differs from FIG. 16 in that the contact surface 622 of the ophthalmological patient interface 6 as shown in FIG. 17 does not have a circular outer contour. The outer contour of the contact surface 622 has an egg shape or has an oval shape.

In a further embodiment, not shown in the figures, the ophthmological patient interface 6 further comprises an opening, for example, in the eye fixation portion 62 and/or in the coupling portion 61, which is configured to supply/dispense coupling liquid to the through opening 63, preferably during the treatment of the eye.

LIST OF REFERENCE SIGNS

100 ophthalmological laser treatment system
1 ophthalmological laser treatment device
2 base station
21 treatment laser source
22 scanner
23 optical module
3 control module
4 arm
41 first arm joint
42 second arm joint
43 third arm joint
5 application head
6 patient interface
61 coupling portion
62 eye fixation portion
621 suction opening
622 rotationally asymmetric contact surface
622*a* cornea contacting element
622*b* sclera contacting element
623 treatment surface
624 sealing
625 protrusion
626 contact body
627 extension portion
628 flat contact surface
629 form-fitted contact body
629*a* form-fitted contact surface
63 through opening
64 suction cup
65 spoon-shaped gripper arm
651 safety coupling 7 optical imaging device
8 monitor
9 person
91 eye of the person
10 optical mirror element
T treatment laser beam
v optical axis of an eye
p main central optical axis of the application head
r central axis of the coupling portion
c central axis of the eye fixation portion
α inclination angle

The invention claimed is:

1. An ophthalmological patient interface for application to an eye of a person, the ophthalmological patient interface comprising:

a. a coupling portion configured to be arranged on an application head of an ophthalmological laser treatment system;

b. an eye fixation portion configured to be arranged on the eye, wherein the eye fixation portion comprises a cornea contacting element, configured to contact at least partially the cornea of the eye, and a sclera contacting element, configured to contact at least partially the sclera of the eye, wherein the cornea contacting element and the sclera contacting element define a rotationally asymmetric contact surface configured to contact the eye; and c. a through opening, extending through the coupling portion and the eye fixation portion, wherein the through opening is configured to enable a treatment laser beam from the application head to pass through the ophthalmological patient interface to penetrate a target volume of tissue of the eye, wherein the rotational asymmetric contact surface has a circular outer contour, and wherein the rotational asymmetry of the rotational asymmetric contact surface is determined by the arrangement of the cornea contacting element and the sclera contacting element within the circular outer contour.

2. The ophthalmological patient interface according to claim 1, wherein the sclera contacting element comprises a rotationally asymmetric suction opening configured to be fluidically connected to a negative pressure, such that the ophthalmological patient interface is firmly positioned on the eye, when the ophthalmological patient interface is applied on the eye and the negative pressure is provided on the suction opening.

3. The ophthalmological patient interface according to claim 1, wherein the negative pressure applied to the suction opening of the cornea contacting element is higher than the negative pressure applied to the suction opening of the sclera contacting element.

4. The ophthalmological patient interface according to claim 1, wherein the suction opening of the cornea contacting element has a partial-ring-shape.

5. The ophthalmological patient interface according to claim 1, wherein at least one of: the cornea contacting element or the sclera contacting element comprises protrusions, which are configured to penetrate tissue of the cornea or the sclera, respectively.

6. The ophthalmological patient interface according to claim 1, wherein the eye fixation portion comprises a flat contact body arranged in the through opening, wherein the flat contact body is at least partially transparent for the treatment laser beam to enable the penetration of the target volume of tissue of the eye, wherein the flat contact body comprises a flat contact surface, which forms part of the rotationally asymmetric contact surface and which is configured to conform the sclera of the eye.

7. The ophthalmological patient interface according to claim 1, wherein the cornea contacting element comprises a form-fitted contact body comprising a form-fitted contact surface forming part of the rotationally asymmetric contact surface, wherein the form-fitted contact surface is form-fitted to a shape of the outer surface of the cornea of the eye, wherein the form-fitted contact surface is configured to be at least partially in form-fitting contact with the cornea of the eye for firmly positioning the ophthalmological patient interface on the eye.

8. The ophthalmological patient interface according to claim 1, wherein at least one of: the cornea contacting element or the sclera contacting element comprise at least one suction cup having a flexible contact body configured to contact the eye, thereby forming part of the rotationally asymmetric contact surface, for positioning the ophthalmological patient interface with respect to the eye.

9. The ophthalmological patient interface according to claim 8, further comprising a bracket arranged between the suction cup and the eye fixation portion, wherein the bracket extends from the eye fixation portion at a specific angle and at a specific length such that the suction cup is configured to contact the cornea of the eye coaxially with respect to the optical axis of the eye.

10. The ophthalmological patient interface according to claim 1, wherein the sclera contacting element comprises at least one spoon-shaped gripper arm extending from the coupling portion or the eye fixation portion, wherein the spoon-shaped gripper arm extends arc-shaped having an eye-ball radius from the eye fixation portion, thereby forming part of the rotationally asymmetric contact surface, for positioning the ophthalmological patient interface with respect to the eye.

11. The ophthalmological patient interface according to claim 10, wherein the ophthalmological patient interface further comprises a safety coupling wherein the safety coupling comprises a first part connected rigidly to the spoon-shaped gripper arm and a second part connected rigidly to at least one of: the eye fixation portion or the coupling portion, wherein the first part is connected detachable to the second part, such that the safety coupling opens when a force, which engages on the ophthalmological patient interface, reaches or surpasses a predefined threshold.

12. The ophthalmological patient interface according to claim 11, wherein the first part and the second part of the safety coupling are connected detachable by means of magnets or by means of a vacuum.

13. The ophthalmological patient interface according to claim 1, wherein the coupling portion and the eye fixation portion of the ophthalmological patient interface are at least two individual parts, which are configured to be coupled together for forming at least partially the ophthalmological patient interface.

14. An ophthalmological patient interface for application to an eye of a person, the ophthalmological patient interface comprising:

a. a coupling portion configured to be arranged on an application head of an ophthalmological laser treatment system, b. an eye fixation portion configured to be arranged on the eye, wherein the eye fixation portion comprises a cornea contacting element, configured to contact at least partially the cornea of the eye, and a sclera contacting element, configured to contact at least partially the sclera of the eye, wherein the cornea contacting element and the sclera contacting element define a rotationally asymmetric contact surface configured to contact the eye, and c. a through opening, extending through the coupling portion and the eye fixation portion, wherein the through opening is configured to enable a treatment laser beam from the application head to pass through the ophthalmological patient interface to penetrate a target volume of tissue of the eye, and wherein the cornea contacting element comprises a rotationally asymmetric suction opening configured to be fluidically connected to a negative pressure, such that the ophthalmological patient interface is firmly positioned on the eye, when the ophthalmological patient interface is applied on the eye and the negative pressure is provided on the suction opening.

15. An ophthalmological patient interface for application to an eye of a person, the ophthalmological patient interface comprising:

a. a coupling portion configured to be arranged on an application head of an ophthalmological laser treatment system, b. an eye fixation portion configured to be arranged on the eye, wherein the eye fixation portion comprises a cornea contacting element, configured to contact at least partially the cornea of the eye, and a sclera contacting element, configured to contact at least partially the sclera of the eye, wherein the cornea contacting element and the sclera contacting element define a rotationally asymmetric contact surface configured to contact the eye, and c. a through opening, extending through the coupling portion and the eye fixation portion, wherein the through opening is configured to enable a treatment laser beam from the application head to pass through the ophthalmological patient interface to penetrate a target volume of tissue of the eye, and wherein the through opening is configured to be at least partially filled with a coupling liquid, wherein at least one of: the cornea contacting element or the sclera contacting element comprises a sealing, and wherein the sealing is configured to seal between the surface of the eye and the ophthalmological patient interface when applied on the eye.

* * * * *